United States Patent [19]

Barrett et al.

[11] 4,288,548

[45] Sep. 8, 1981

[54] PROCESS FOR ISOMERIZING GLUCOSE TO FRUCTOSE

[75] Inventors: Steven P. Barrett, Byron, Ill.; William J. Nelson, Camanche, Iowa

[73] Assignee: Standard Brands Incorporated, New York, N.Y.

[21] Appl. No.: 94,520

[22] Filed: Nov. 15, 1979

[51] Int. Cl.³ .............................................. C12P 19/24
[52] U.S. Cl. ..................................................... 435/94
[58] Field of Search .......................................... 435/94

[56] References Cited

U.S. PATENT DOCUMENTS

Re. 28,885  6/1976  Cotter et al. ........................... 435/94
3,806,363  4/1974  Takasaki et al. ................... 127/46 A

OTHER PUBLICATIONS

Advances in Carbohydrate Chemistry, vol. 19, pp. 212–213 (1964).
Die Starke, vol. 26, No. 10, pp. 350–356 (1976).

Primary Examiner—Lionel M. Shapiro
Attorney, Agent, or Firm—Richard Kornutik; Henry S. Wyzan; Robert A. Conzett

[57] ABSTRACT

A glucose-containing liquor is treated with an ion exchange material in the bisulfite/sulfite form and the treated liquor contacted with immobilized glucose isomerase to convert a portion of the glucose to fructose.

9 Claims, No Drawings

PROCESS FOR ISOMERIZING GLUCOSE TO FRUCTOSE

BACKGROUND OF THE INVENTION

1. Field of the Invention

This invention relates to a process for isomerizing glucose in a glucose-containing liquor to fructose. More particularly, this invention relates to a process for treating a glucose-containing liquor with an ion exchange material and then contacting the treated liquor with immobilized glucose isomerase to convert a portion of the glucose to fructose.

The use of microbial and fungal enzymes adsorbed onto or bonded to inert carriers to provide immobilized biological catalysts has largely superseded older methods whereby soluble enzymes or whole cells of microorganisms were utilized. In general, immobilized enzymes provide a number of significant advantages over soluble or cell-bound enzymes particularly in commercial systems for carrying out continuous conversion processes. Because of the economics of these systems, it is of the utmost importance that the enzymes not be substantially inactivated or denatured by the process used to affect immobilization. It is equally important that the conditions under which the immobilized enzymes are utilized are such that the stability of the enzymes is maintained over a period sufficient to permit conversion of large quantities of substrate. Thus, for example, the presence in the substrate of materials which in some manner interfere with or inactivate glucose isomerase may have a deleterious effect on the stability of the immobilized enzyme and shorten its effective life to a significant degree.

Generally, prior to isomerization, glucose-containing liquors are refined by conventional means, e.g., by treating the liquors with carbon and ion exchange materials in order to remove interferring metals and carbohydrate by-products which might inactivate or denature glucose isomerase in an uneconomically short period. It has been found, however, that although such treatments provide some prolongation of the effective life of immobilized glucose isomerase, the stability of the enzyme is not as great as is desirable in continuous processes for isomerizing glucose to fructose.

2. Discussion of the Prior Art

U.S. Pat. No. Re. 28,885 to Cotter et al. relates to an enzymatic method for isomerizing glucose syrups utilizing soluble glucose isomerase or cellular material containing this enzyme. Incorporation of a source of $SO_2$ into glucose-containing liquors during isomerization is taught to reduce denaturation of the glucose isomerase and to inhibit undesirable color formation in the finished product. Cotter et al. disclose that it is preferred to provide soluble salts of sulfurous acids in the glucose-containing liquor before the isomerization process is initiated in order to obtain the full benefit of their presence. It is also disclosed in U.S. Pat. No. Re. 28,885 that levels of $SO_2$ effective to inhibit undesirable color formation in the finished product may be provided by passing the liquor through ion exchange resins in the sulfite form.

German Pat. No. 2,160,919 to Takasaki teaches a process for the separation of a mixture of carbohydrates by treating the mixture with an anion exchanger in the sulfite or bisulfite form.

Anet in *Adv. Carbohydrate Chem.*, Vol. 19, pp. 212-213 (1964) discloses that the inhibition of non-enzymatic browning in foods by sulfite depends, in part, on the capture of various reactive intermediates and their conversion to carbonyl-bisulfite addition compounds of sulfonic acids.

In *Die Starke*, 26 Jahrg., 1976/Nr.10, pp. 350-356, Oestergaard et al. recommend that glucose-containing substrates be filtered and treated with carbon and ion-exchange materials prior to carrying out continuous isomerizations with glucose isomerase to remove impurities which may adversely affect the activity of the enzyme. They further disclose that possibly harmful enzyme contaminants in the syrup, which apparently are formed during isomerization, may be protected against by utilizing a particular arrangement of a plurality of columns containing the immobilized glucose isomerase.

OBJECTS OF THE INVENTION

It is a principal object of the present invention to provide a process for treating a glucose-containing substrate whereby the stability or effective life of immobilized glucose isomerase utilized to convert a portion of the glucose to fructose is increased.

It is also an object of the present invention to provide a process for treating a glucose-containing substrate with ion exchange material in the bisulfite/sulfite form whereby the stability or effective life of immobilized glucose isomerase utilized to convert a portion of the glucose to fructose is increased.

It is a further object of the present invention to provide a process for treating a glucose-containing substrate with anion exchange resin in the bisulfite/sulfite form whereby the stability or effective life of immobilized glucose isomerase utilized to convert a portion of the glucose to fructose is increased.

These and other objects will be apparent from the description of the invention and the appended claims.

SUMMARY OF THE INVENTION

A glucose-containing liquor is treated with ion exchange material in the bisulfite/sulfite form and the treated liquor contacted with immobilized glucose isomerase to convert a portion of the glucose in the liquor to fructose.

DETAILED DESCRIPTION OF THE INVENTION

Glucose-containing solutions are usually produced by treating starch by one of three methods. In the first method an acid is utilized at relatively high temperatures to hydrolyze the starch; in the second, starch is first liquefied by an acid treatment and then saccharification is effected by enzymatic means; in the third method both liquefaction and saccharification are effected by enzymatic means. The acid-enzyme and enzyme-enzyme processes are most widely practiced in the industry.

The stability or effective life of immobilized glucose isomerase is probably influenced to the greatest extent by the quality of the substrate. The quality of glucose-containing liquors produced in the corn wet milling industry may be highly variable. Generally, these liquors are refined by conventional methods prior to isomerization and U.S. Pat. No. Re. 28,885 teaches additionally that the presence of small amounts of $SO_2$ in glucose-containing liquors during isomerization reduces denaturation of soluble or intracellular glucose isomerase as well as inhibiting color formation in the finished syrup.

Although the prior art methods have proven to be beneficial to a degree, continuous isomerization processes utilizing immobilized glucose isomerase have not hitherto been as efficient as desired due to the fact that the enzyme becomes inactivated after a relatively short period of use.

It has now been found that when glucose-containing liquors, which have been treated with carbon and ion exchange material in a conventional manner, are contacted with an ion exchange material in the bisulfite/sulfite form and the contacted liquors subsequently isomerized with immobilized glucose isomerase, the stability or effective life of the immobilized enzyme is substantially increased over that attained by prior art processes. This finding is surprising in view of the fact that the concentration of $SO_2$ in the resin-contacted liquors is similar to that taught by the prior art to be effective in reducing denaturation of soluble or intracellular glucose isomerase. In other words, the improvement in enzyme stability is not due to leaching or displacement of soluble bisulfite/sulfite from the resin bed into the liquor.

A number of types of ion exchange materials may be utilized in the present process, the only requirement being that they be capable of being converted to the bisulfite/sulfite form. Exemplary of such materials are anion exchange cellulose and Sephadex and anion exchange resins. Resins are preferred since they can simply be placed in a column or columns and the glucose solution passed therethrough in a continuous manner. Moreover, they can be relatively easily regenerated. The preferred resins are of the weak base and strong base types. Exemplary of suitable strong base resins are Dowex 1, 2 and 21K (Dow); Duolite A-101D and A-102 (Diamond Shamrock); Ionac A-535 and A-540 (Ionac) and Amberlite IRA-900 (Rohm & Haas). Suitable weak base resins are exemplified by Duolite A-6, A-7, A-30B and ES-561 (Diamond Shamrock) and Ionac A-300 (Ionac).

The preferred resins are those in which the matrix is principally composed of polystyrene and which have a relatively low degree of cross-linking.

In order to convert the resin to the bisulfite/sulfite form, it is preferred that the resin first be in the OH form. This may be accomplished by treating the resin with a suitable hydroxide. After washing to remove excess salts, the resin can be contacted with a source of sulfite and bisulfite ions. Solutions of salts which will provide a source of these ions may be utilized. Exemplary of suitable salts are sodium and potassium sulfite and sodium and potassium bisulfite. In general, excess quantities of these salts will be used to convert the resin to the desired form to insure that the full exchange capacity of the resin is achieved. Thereafter, the resins are rinsed or otherwise washed to remove the excess generant.

In solutions, an equilibrium exists between the bisulfite and sulfite ions. At a pH value of about 7, these ions will be present in about equal amounts, but at lower pH values the bisulfite form is favored. Thus, it should be understood that the expression "bisulfite/sulfite" should not be construed to mean that the form of the exchanger is such that bisulfite and sulfite are present in any specific proportions but that, to some degree, the resin exists in both forms.

The conditions under which the glucose-containing liquor is contacted with the resin may vary widely but, typically, the pH of the solution will be in the range of from about 1.0 to about 8.0 and preferably from about 3.5 to about 6.5. The temperature at which the liquor may be passed through a bed or column of resin may also vary but such should not be so high as to result in substantial production of degradation products or to deleteriously affect the functionality of the resin. It has been reported that the preferred resins are adversely affected at temperatures of above 80° C. Temperatures in the range of from about 25° to about 70° C. have provided satisfactory results. The preferred temperature range is from about 50° to about 65° C.

The presence of enzyme activators is generally desirable during enzymatic isomerization processes. In commercial practice, small amounts of salts such as $MgSO_4$ and $NaHSO_3$ are typically added to the substrate prior to isomerization for this purpose.

Although the flow rate at which the liquor is passed through a column or columns of the resin is not critical, satisfactory results have been obtained at a rate of from about 0.08 to about 0.21 gal/min/ft$^3$ of resin. The liquor may be passed through the column or columns in an up-flow or a down-flow direction.

Since different facilities for producing glucose-containing liquors may operate under somewhat different conditions, the composition of such liquors is subject to some degree of variability. It is difficult, therefore, to quantify the relationship between the extent of resin treatment and the increase in stability or effective life of immobilized glucose isomerase obtained. Obviously, to efficiently achieve the objects of the present invention, the resin must be contacted with a sufficient amount of a source of bisulfite and sulfite ions under conditions such that the treated resin will not become exhausted in an uneconomically short period.

ANALYTICAL METHODS

Determination of $SO_2$ concentration

Sulfur dioxide in the liquors was determined as follows: A sample of the liquor in the range of 50–60 g was weighed accurately into a dish and transferred quantitatively into an 800 ml Kjeldahl flask employing 300 ml of distilled water. Ten ml of concentrated phosphoric acid was added followed by 1 g of sodium bicarbonate. The flask was immediately connected to a standard Kjeldahl distillation apparatus and approximately 250 ml distilled into a Erlenmeyer flask containing 25 ml of water and 10–12 ml of 0.8 percent sodium hydroxide solution. When the distillation was complete, the distillate was acidified with phosphoric acid and 2 ml of starch paste indicator added. The solution was then titrated with 0.0625 N iodine solution (1 ml equivalent to 0.002 g of $SO_2$) until a blue color persisted for 1 minute. Percent $SO_2$ dry basis was calculated as follows:

$$\text{Percent } SO_2 = \frac{\text{titre (ml)} \times 0.002}{\text{Sample wt. (g)} \times \text{Dry Substance (\%)}}$$

Determination of stability (half-life) of immobilized glucose isomerase

An amount of immobilized glucose isomerase having an enzyme activity of 1000 IGIU was placed in a jacketed glass column (2.5×30 cm) outfitted in a conventional manner. Before being placed in the column, the immobilized enzyme preparation was stirred with the substrate solution under vacuum to remove entrapped air. The substrate which comprised a deareated glucose-containing liquor obtained by enzymatic liquefication and saccharification of corn starch was passed continuously through the column under the isomerization conditions enumerated in example I, below. The column effluent was sampled daily and the flow rate, pH at room temperature and percent fructose determined.

The half-life of the immobilized glucose isomerase was determined by substitution of the appropriate values into the following formula and solving graphically for $\tau$ and $K_f$:

$$\ln\left(\frac{I_e - I_o}{I_e - I}\right) = \frac{K_f E_t (e^{-0.693 \Delta t/\tau})}{CR}$$

$\Delta t$ = Change in time (hours)
$I_o$ = Degree of isomerization of reactor feed, F/(F+G) where F and G are concentrations of fructose and glucose, respectively, (g/ml)
$I$ = Degree of isomerization of reactor effluent, F/(F+G)
$I_e$ = I at equilibrium (0.514 at 65° C.)
$K_f$ = Initial reaction rate constant, g (G+F) hr$^{-1}$ IGIU$^{-1}$
$E_t$ = Total enzyme in the reactor (IGIU's)
C = Substrate concentration, glucose (g/ml)
$\tau$ = Half-life of enzyme (hours)
R = Flow Rate (ml/hr)

Determination of Activity of Immobilized Glucose Isomerase

The activity (IGIU) of immobilized glucose isomerase was determined by the method set forth in U.S. Pat. No. 4,111,750 to Colilla et al.

In order to more clearly describe the nature of the present invention, specific examples will hereinafter be described. It should be understood, however, that this is done solely by way of example and is not intended to delineate the scope of the invention or limit the ambit of the appended claims.

EXAMPLE I

This example illustrates the utilization of a weak base anion exchange resin in the bisulfite/sulfite form to carry out the process of the present invention.

1760 ml of Duolite ES-561 anion exchange resin (weak base) was placed in a column having an inside diameter of 8 cm and a height of 39 cm. The following steps were employed to activate the resin. In each step, the reagents were passed upwardly through the resin column.

1. Resin column was backwashed with deionized water to remove resin fines.
2. 3500 ml of a 7 percent HCl solution was passed through the column at a rate of 10 ml/min.
3. Resin column was rinsed with about 6000 ml of deionized water until the effluent pH was greater than 4.
4. 3000 ml of a 4 percent NaOH solution was passed through the column at a rate of 10 ml/min.
5. Resin column was rinsed with deionized water until effluent pH was less than 10.
6. 4600 ml of 1 N NaHSO₃ was passed through the column at a rate of 10 ml/min.
7. Resin column rinsed with deionized water until the effluent pH was about 5.5.

The activated resin was placed in two columns having an inside diameter of 8 cm. and a height of 39 cm. and two samples of refined glucose-containing solutions (carbon treated and resin deionized) prepared by the enzyme-enzyme method were passed through the columns at room temperature, inlet pH of 4.5 and at a rate of about 1 ml/min in an upward flow direction.

The carbohydrate composition of the glucose-containing solutions before and after treatment with the resins was determined and is set forth in Table I below.

TABLE I

Analysis of Glucose-Containing Solutions Treated with Regenerated Duolite ES-561 Anion Exchange Resin

| Sample Designation | Percent Dry Basis | | | | |
| --- | --- | --- | --- | --- | --- |
| | Maltulose[1] | Dextrose[2] | DP$_{2-4}$[2] | DP$_{5+}$[2] | Fructose[2] |
| A. Control (no treatment) | 0.3 | 94.2 | 2.9 | 3.0 | 0 |
| A. Resin Treated | 0.3 | 94.2 | 2.7 | 3.0 | 0 |
| B. Control (no treatment) | not determined | 93.5 | 3.1 | 2.6 | 0.7 |
| B. Resin Treated | not determined | 93.3 | 3.3 | 2.7 | 0.7 |

[1] by Gas-Liquid Chromatography
[2] by Liquid Chromatography

From the above table, it is apparent that the resin treatment of the solutions had no effect on the carbohydrate composition thereof when compared to the control samples.

Glucose isomerase was immobilized on DEAE cellulose in accordance with the procedure described in U.S. Pat. No. 3,909,354 to Thompson et al. and the immobilized enzyme preparation packed into two jacketed columns.

The conditions utilized for isomerization were as follows:

| | |
| --- | --- |
| Temperature | 65° C. |
| Substrate Glucose Concentration | 50% (d.b.) |
| Flow Rate | 0.42 ml/min. |
| MgSO₄. 7H₂O | 0.005 M |
| NaHSO₃ | 0.005 M. |
| pH at 25° C. at column inlet | 7.8 |

Resin treated (Duolite ES-561) and untreated glucose-containing solutions were passed separately through the columns. The results are set forth in Table II below.

TABLE II

Effect of Treating Glucose-Containing Substrate
with Duolite ES-561 on Stability of
Immobilized Glucose Isomerase

| | Substrate | |
|---|---|---|
| | Control | Resin Treated |
| Initial Column Activity (IGIU) | 1066 | 1065 |
| Half-Life of Immobilized Glucose Isomerase (hours) | 288 | 696 |

The above data demonstrate that treatment of a glucose-containing solution with a resin in the bisulfite/sulfite form greatly improves the effective life of immobilized glucose isomerase.

EXAMPLE II

This example illustrates the preparation and utilization of a strong base anion exchange resin in the bisulfite/sulfite form to carry out the process of the present invention.

960 ml of Amberlite IRA-900 resin was placed in a column having an inside diameter of 8 cm and height of 39 cm. The following steps were employed to activate the resin. In each step the reagents were passed upwardly through the resin column.

1. 3000 ml of a 4 percent NaOH solution was passed through the column at a rate of 10 ml/min.
2. Resin column was rinsed with about 5000 ml of deionized water at a rate of 10 ml/min.
3. 3000 ml of 1 N $NaHSO_3$ was passed through the column.
4. 5000 ml of deionized water was passed through the column at a rate of 10 ml/min to remove excess $NaHSO_3$.

The activated resin was placed in a column having an inside diameter of 8 cm and a height of 39 cm and a glucose-containing solution obtained from a commercial corn wet milling operation was passed through the bed at a rate of about 6 ml/min. After the resin treatment, the liquor was Millipore filtered (0.45μ pore size) to remove any microbial contamination which may have formed in the column.

Isomerization tests were carried out in accordance with the procedure described in Example I. The results are set forth in Table III below.

TABLE III

Effect of Treating Glucose-Containing Substrate
with Amberlite IRA-900 on Stability of
Immobilized Glucose Isomerase

| | Substrate | |
|---|---|---|
| Isomerase | Control | Resin Treated |
| Initial Column Activity (IGIU) | 920 | 918 |
| Half-Life of Immobilized Glucose Isomerase (hours) | 321 | 702 |

The prior art teaches that incorporation of small amounts of a source of $SO_2$ into the glucose-containing substrate during isomerization with glucose isomerase reduces denaturation of the enzyme. Thus, in U.S. Pat. No. Re. 28,885 it is disclosed that $SO_2$ levels of from 0.02 to 0.3 percent, dry basis, in the glucose-containing substrate prolonged the effective life of glucose isomerase. An experiment was carried out (Example III) to determine whether the improved stability of immobilized glucose isomerase affected by the present process was due to the presence of soluble bisulfite/sulfite leached from the column or bed of the ion exchange material.

EXAMPLE III

This example illustrates the amount of leaching into solution of soluble bisulfite/sulfite which occurs when a glucose-containing liquor is passed through an ion exchange resin in the bisulfite/sulfite form.

A bed of a strong base anion exchange resin (Amberlite IRA-900) contained in a column having the dimensions 49.2×0.6 inches was converted to the bisulfite/sulfite form by passage therethrough of 2 bed volumes of 1 M $NaHSO_3$ at a flow rate of 4.3 ml/min. The bed was then rinsed with one bed volume of deionized water at the same flow rate. A glucose-containing solution comprising a refined enzyme-enzyme cornstarch hydrolysate having a dry solids content of 45 percent and containing about 93 percent glucose on a dry basis was passed through the bed at a flow rate of 4.2 ml/min. The temperature of the column was maintained at 60° C. and the pH of the solution was 5.5, measured at room temperature.

The glucose-containing solution was passed through the column continuously for 120 hours and the $SO_2$ content of the effluent was measured periodically.

The amounts of soluble bisulfite/sulfite leached from the resin into the solution at various sampling periods are shown in Table IV, below, in terms of the $SO_2$ concentration (dry solids basis) at the sampling periods noted in the table.

TABLE IV

| Effluent Sampling Period (hours) | Effluent $SO_2$ Conc. (%, d.b.) |
|---|---|
| 18 | 0.026 |
| 42 | 0.032 |
| 66 | 0.060 |
| 90 | 0.010 |
| 114 | 0.007 |

The data in the above table demonstrate that the level of bisulfite/sulfite leached into the solution did not exceed about 0.06 percent in terms of $SO_2$ concentration. It is apparent, therefore, that the treated resin cannot serve as a source of $SO_2$ in sufficient quantity to cause the observed increase in the stability of immobilized glucose isomerase over that attained by prior art methods.

EXAMPLE IV

This example illustrates the effect on the stability of immobilized glucose isomerase of incorporating increasing amounts of sodium bisulfite into a glucose-containing solution.

Immobilized glucose isomerase was prepared by adsorbing a solution of Streptomyces sp. glucose isomerase onto DEAE cellulose as described in U.S. Pat. No. 3,788,945 to Thompson et al. The immobilized preparation had an activity of 384.4 IGIU per gram, dry basis. A substrate solution was prepared comprising a refined enzyme-enzyme hydrolyzate of cornstarch containing about 93 percent glucose on a dry basis. Varying amounts of sodium bisulfite were added to portions of the substrate solution prior to final pH adjustment and the portions passed separately through columns of the immobilized enzyme under the following isomerization conditions:

| | |
|---|---|
| Substrate concentration | 50% d.s. |
| Temperature | 68.8° C. |
| pH | 7.25 at 27° C. |
| Flow rate | 0.45 ml min$^{-1}$ |
| MgSO$_4$ | 0.005M in substrate |
| CoCl$_2$ | 0.0005M in substrate |
| Enzyme | Plug of 1.6 g immobilized glucose isomerase mixed with 3.2 g chemical cellulose |
| Time of operation | ~200 hours |
| SO$_2$ concentrations in substrate (%, d.b.) | 0.06, 0.10, 0.30, 0.50 and 1.00 |

The results are shown in Table V below:

TABLE V

Effect of Varying Concentrations of SO$_2$ in Glucose Substrate on Stability of Immobilized Glucose Isomerase

| Substrate Portion | SO$_2$ Conc. (%, d.b.) | Halflife of Immob. G.I. (hours) |
|---|---|---|
| 1 | 0.06 | 210 |
| 2 | 0.10 | 213 |
| 3 | 0.30 | 285 |
| 4 | 0.50 | 347 |
| 5 | 1.00 | 398 |

The data in the above table demonstrate that an increase of SO$_2$ in the glucose liquor from 0.06 to 0.10 percent results in an insignificant increase in enzyme half-life. Treatment with resin in the bisulfite/sulfite form increases the SO$_2$ in the glucose liquor by about 0.01 to 0.06 percent, as shown in example III. It is clear, therefore, that the marked improvement in the enzyme half-life when the glucose liquor is treated with resin in the bisulfite/sulfite form is not due to leaching of the SO$_2$ from the resin into the glucose liquor. Although the reason for the improvement is not completely understood, it may be that the resin treatment removes or inhibits the effect of certain unidentified enzyme inactivators which may be present in the glucose syrups and thus results in increased enzyme half-life.

EXAMPLE V

This Example illustrates the utilization of a strong base anion exchange resin in the bisulfite/sulfite form in glucose isomerization reactions carried out with two types of immobilized glucose isomerase.

Amberlite IR-900 in the bisulfite/sulfite form activated according to the procedure described in Example II was placed into four 60 cm by 2.5 cm columns. Each column contained about 0.0083 ft$^3$ of resin. The columns were connected in series and maintained at a temperature of about 40°±2° C. A commercial glucose-containing solution, enzymatically liquefied and saccharified, was passed through the resin columns at a flow rate of 12–16 ml/min.

Isomerization tests were carried out in accordance with the procedure described in Example I using two different types of immobilized glucose isomerase. The results are set forth in Table VI below.

TABLE VI

Effect of Treating a Glucose-Containing Substrate with a Strong Base Anion Exchange Resin in the Bisulfite/Sulfite Form on Stability of Two Types of Immobilized Glucose Isomerase

| Type of Immobilized Glucose Isomerase | Substrate | Column Activity (IGIU) | Approximate Half-Life of Immobilized Glucose Isomerase (hours) | Flow-Through Period (hours) |
|---|---|---|---|---|
| Novo Sweetzyme Type S | Control (no resin treatment) | 1018 | 334 | 402.5 |
| Novo Sweetzyme Type S | Resin Treated | 1018 | 523 | 331 |
| Glucose Isomerase Immobilized on DEAE Cellulose (U.S. Pat. No. 3,909,354) | Control (no resin treatment) | 1000 | 233 | 402.5 |
| Glucose Isomerase Immobilized on DEAE Cellulose (U.S. Pat. No. 3,909,354) | Resin Treated | 1000 | 643 | 331 |

The data in the above table demonstrate that treating a glucose-containing substrate with a strong base anion exchange resin effectively prolongs the life of immobilized glucose isomerase prepared by different methods.

The terms and expressions which have been employed are used as terms of description and not of limitation, and it is not intended in the use of such terms and expressions to exclude any equivalents of the features shown and described or portions thereof since it is recognized that various modifications are possible within the scope of the invention claimed.

What is claimed is:

1. A process for enzymatically isomerizing glucose in an ion exchange refined glucose-containing liquor to fructose comprising treating said refined liquor with an ion exchange material in the bisulfite/sulfite form and contacting the treated liquor with immobilized glucose isomerase under glucose isomerizing conditions to convert a portion of the glucose to fructose.

2. The process defined in claim 1, wherein the ion exchange material is an anion exchange resin in the bisulfite/sulfite form.

3. The process defined in claim 2, wherein the ion exchange material is a weak base anion exchange resin in the bisulfite/sulfite form.

4. The process defined in claim 2, wherein the ion exchange material is a strong base anion exchange resin in the bisulfite/sulfite form.

5. The process defined in claim 1, wherein the pH at which the glucose-containing liquor is treated with the resin is in the range of from about 1.0 to about 8.0.

6. The process defined in claim 5, wherein the pH at which the glucose-containing liquor is treated with the resin is in the range of from about 3.5 to about 6.5.

7. The process defined in claim 1, wherein the glucose-containing liquor is treated with the resin at a temperature of below about 80° C.

8. The process defined in claim 7, wherein the glucose-containing liquor is treated with the resin at a temperature in the range of from about 25° to about 70° C.

9. The process defined in claim 8, wherein the glucose-containing liquor is treated with the resin at a temperature in the range of from about 50° to about 65° C.

* * * * *